United States Patent
Garver et al.

[11] Patent Number: 6,134,952
[45] Date of Patent: Oct. 24, 2000

[54] DISSOLVED SOLID ANALYZER

[75] Inventors: Theodore M. Garver, Edmonton; Kenneth Boegh, Thunder Bay, both of Canada

[73] Assignee: Alberta Research Council Inc., Edmonton, Canada

[21] Appl. No.: 09/157,145

[22] Filed: Sep. 18, 1998

[30] Foreign Application Priority Data

Sep. 18, 1997 [CA] Canada ................................ 2216046

[51] Int. Cl.⁷ .............................................. G01N 15/06
[52] U.S. Cl. ...................... 73/61.71; 73/61.48; 324/693; 356/441; 162/49
[58] Field of Search ............................... 73/53.03, 61.71, 73/61.48; 324/693; 250/373; 356/441, 442; 162/49–61, 83

[56] References Cited

U.S. PATENT DOCUMENTS

| | | | |
|---|---|---|---|
| 4,012,197 | 3/1977 | Howarth | 162/49 |
| 4,046,621 | 9/1977 | Sexton | 162/40 |
| 4,096,028 | 6/1978 | Rosenberger | 162/49 |
| 4,318,180 | 3/1982 | Lundqvist et al. | 364/555 |
| 4,752,131 | 6/1988 | Eisenlauer et al. | 356/338 |
| 4,791,305 | 12/1988 | Karaila | 250/574 |
| 4,886,576 | 12/1989 | Sloan | 162/49 |
| 4,895,618 | 1/1990 | Tikka et al. | 162/49 |
| 4,999,514 | 3/1991 | Silveston | 250/575 |
| 5,453,832 | 9/1995 | Joyce | 356/338 |
| 5,547,012 | 8/1996 | Marcoccia et al. | 162/42 |

FOREIGN PATENT DOCUMENTS

| | | |
|---|---|---|
| 1268605 | 5/1990 | Canada . |
| 2106472 | 3/1992 | Canada . |
| 2106472 | 10/1992 | Canada . |
| 2090820 | 3/1993 | Canada . |
| 2174432 | 10/1994 | Canada . |
| 2174432 | 4/1995 | Canada . |
| WO91/17305 | 11/1991 | WIPO . |

Primary Examiner—Michael Brock
Attorney, Agent, or Firm—Neil Teitelbaum & Associates

[57] ABSTRACT

On-line measurements of an amount of dissolved solids in a liquid sample are determined by using both conductivity and UV measurements. More particularly, an amount of dissolved solids in a pulp and paper mill process water or effluent is determined by irradiating at least a portion of a liquid sample with ultraviolet light and subsequently measuring an absorption of the light by the liquid sample. Furthermore the conductivity of the liquid sample is measured and subsequently a computation is from a first relationship between the measured absorption of the first wavelength by the liquid sample and the measured conductivity of the liquid sample using a suitably programmed processor.

25 Claims, 12 Drawing Sheets

DISSOLVED SOLID ANALYZER

FIELD OF THE INVENTION

This invention relates to the application of conductivity and UV measurements for on-line measurements of an amount of dissolved solids in a liquid sample. More particularly, an aspect of the invention relates to the determination of the amount of dissolved solids in a pulp and paper mill process water or effluent using a combination of conductivity and UV absorbance measurements.

BACKGROUND OF THE INVENTION

On-line measurements of the amount of dissolved solids of paper mill process waters, such as whitewater, graywater, and effluents, can provide the necessary feedback for optimizing retention, flocculation, and water flow in the paper mill. At present, on-line measurements do not provide the detail necessary for optimal control. This is particularly the case when measuring the total amount of dissolved solids in a liquid sample.

The importance of the management of the composition of industrial water streams is described by Simons, NLK Consultants, and Sandwell Inc., in a 1994 publication "Water Use Reduction in the Pulp and Paper Industry", Canadian Pulp and Paper Association, Montreal. The excessive build-up of dissolved solids in a process water stream may decrease process efficiency and increase corrosion, foaming, odour, pitch, precipitation, and scaling. A counter-current flow of water to pulp streams is a commonly used method to efficiently use water in pulp processing and papermaking to optimize the removal of dissolved solids. In order to prevent production problems related to the build-up of dissolved solids in process water it is necessary to efficiently remove and minimize the variation of dissolved solids in liquid samples. Garver et al. in a Journal entitled Tappi Vol. 80 Number8, pages 163–173, 1997 teach that the temporal or spatial variation in the amount of dissolved solids in a water stream may lead to manufacturing problems including precipitation, deposition, scaling and pitch formation.

One standard method for the examination of water and wastewater employed by the American Health Association measures the total amount of dissolved solids directly by gravimetric analysis after evaporation of a known volume of liquid after filtration.

The empirical estimation of dissolved solids using a conductivity measurement is an established technique employing a calibration between the dissolved solids and a conductivity measurement. This method is widely used as a relative measure of dissolved inorganic salts and many conductivity/TDS (Total Dissolved Solids) meters are available on the market. The relationship between dissolved solids and conductivity differs for each type of ion depending on the charge and size of the ion. Empirical constants to convert conductivity (mS cm$^{-1}$) to dissolved solids (mg L$^{-1}$) may vary considerably, i.e. between 0.55 and 0.9 depending on ion type, concentration and temperature, American Public Health Association, Standard Methods for the Examination of Water and Wastewater, American Public Health Association, American Water Works Association, Water Pollution Control Federation, Washington D.C. 1992, pp. 2–47. However, the amount of dissolved solids measured by conductivity is only reliable when specific inorganic salts dominate the dissolved solids present in the water. Conversely, conductivity measurements present a poor measure of the amount of dissolved solids when substances with little or no ionic charge contribute substantially to the amount of dissolved solids.

The principle disadvantages of using conductivity as a measure of the amount of dissolved solids are related to inaccuracies arising from the differences in the specific conductivity of different ions, association or chelation of positive or negative ions resulting in inactive ions, and the poor detection of organic acids and organic neutral substances. In a paper mill situation the relative ratio of dissolved inorganic salts to dissolved organic material varies dramatically depending on the location in the pulp processing sequence. For example, in a lignin retaining pulp brightening process, such as sodium hydrosulfite bleaching, the variation in the amount of dissolved solids may be largely related to the amount of bleach applied and the residual sulfur species resulting from hydrosulfite decomposition.

The patent literature describes applications using conductivity measurements to control water introduction, counter-current flow or sewer flow in pulp or paper processing. The objective of the control of the amount of dissolved solids using conductivity measurements has been to improve the washing, separation and removal of solids and to minimize scaling and deposition. Rosenberger (U.S. Pat. No. 4,096,028) discloses feed-forward control of the amount of dissolved material in a counter-current flowing liquid using conductivity measurements and flow rates. Sexton (U.S. Pat. No. 4,046,621) disclosed a feed backwards method for the control of pulp treatment using conductivity measurements. Heoksema et al. disclose an apparatus for conductivity measurements of pulp washing liquors from a drum type washer. Lisnyansky and Blaecha taught a control strategy for optimizing the efficiency of counter-current flow pulp washing based on a dilution factor or soda wash.

In a counter-current flow pulp treatment or washing not only the removal of dissolved ions may be controlled by a conductivity measurement but the accumulation of the water may also be measured and controlled. The benefits of maintaining a low or constant amount of dissolved solids are related to solubility equilibria which influence the extraction of unwanted material from pulp and also govern the deposition and precipitation reactions leading to unwanted scale and deposits.

The absorbance from selected wavelengths of the UV may be used as a measure of the relative quantity of extractives and lignin or carbohydrate derived components. Marcoccia et al. (U.S. Pat. No. 5,547,012) teach a method of control of kraft pulping by controlling the amount of dissolved organic material in a continuous digestor.

Sloan (U.S. Pat. No. 4,886,576) teaches a method for using the UV absorbance of lignin dissolved during digester cooking for control of pulp cooking parameters and refiner energy. Manook et al. (U.S. Pat. No. 5,420,432 or Cdn. U.S. Pat. No. 2,106,472) disclose an organic pollutant monitor based on UV absorbance measurements for the determination of the amount of organic matter.

Papermaker's demands for high speed and efficiency, flexible manufacturing, stringent quality standards, and environmental compatibility coupled with new developments in on-line process control are driving the development of new sensor technology for the paper machine wet-end. The need for better means for providing wet-end chemistry control is emphasized by recent reports that only 10% of the world's 150 newsprint paper machines operate at above 88% efficiency and over 60% operate under in the low efficiency range of below 82.5%. (Mardon, J., Chinn, G. P., O'Blenes, G., Robertson, G., Tkacz, A. Pulp and Paper Canada, 99(5) 43–46. (1998).

Nazair and Jones teach that wet-end variability arising from practical determinants and disturbances leads to variations in molecular and colloidal interactions that result in practical consequences in terms of the process and the product (Nazair, B. A; Jones, J. C. (Paper Technology 32(10) 37–41. 1991. Optimizing wet-end chemistry—the practicalities.). Practical determinants include the type of furnish, fillers, chemical being used, addition rates, addition points, refining, pH, temperature and consistency. Disturbances include broke, machine breaks, quality of materials, machine wear and seasonality. These variations may deleteriously effect system cleanliness, runability, first pass retention and product quality factors including formation, sizing, uniformity, strength, porosity and defects. The high capital cost of paper machines demands maximization of paper machine efficiency and quality. The papermaker will attempt to minimize system-input variation and counteract variation in practical determinants and disturbances so as to minimize variation and degradation of process efficiency and product quality.

The consequences of poor control of the variation, total level and composition of dissolved substances have been recognized by numerous authors. Gill teaches the importance of variation control of dissolved and colloidal substances in the paper machine wet-end. "Dissolved and colloidal substances (DCS) are released from the water phase from contaminated pulps or broke, and form deposits at the wet-end, press section, machine fabrics and rolls. These deposits cause: downtime; defective products; sheet breaks; frequent fabrics change." William E. Scott address problems related to wet-end chemistry control. *Principles of Wet End Chemistry*. Tappi Press, Atlanta, 1996. p 3. "Deposits and scale usually arise from out-of-control wet end chemistry. Typical examples include chemical additive overdosing, charge imbalances, chemical incompatibility and the shifting of chemical equilibria. All of these phenomena can lead to the formation of precipitates or colloidal aggregates that produce deposits and scale. While there are numerous approaches to treating the symptoms of deposits the best approach is to determine what is out of control and fix it."

One simple measure of the variability of the wet-end system chemistry is the level of dissolved organic and inorganic solids in the paper machine white water system. Tools that have become available for wet-end chemistry monitoring include retention monitoring, turbidity and electrokinetic potential (streaming current, cation charge demand, and zeta-potential) instruments. On-line instrumentation for monitoring and controlling the inorganic and organic dissolved and colloidal solids in a paper mill is at present limited to conductivity measurement or on-line charge measurement. While off-line total dissolved solids, turbidity, pitch counts, COD and TOC measurements may be used. In summary, the presently available means for on-line monitoring of wet-end chemistry fall short of providing reliable measurement of dissolved organic and inorganic solids.

Chemicals can provide control of the levels of DCS and deposit formation can be eliminated or reduced to tolerable levels by careful control of water flow and addition of chemicals for either dispersing or adsorbing and coagulating dissolved and colloidal substances. (Gill, R. S. Paper Technology, 37, July/August, 1996. 23–31. Chemical control of deposits-scopes and limitations.)

It is an object of the present invention to provide a method and an apparatus for on-line measurement of the amount of dissolved solids in a liquid sample, such as in a pulp or paper mill process water or effluent.

It is another object of the invention to provide an analyzer for total dissolved solids by combining conductivity and UV measurements of a liquid sample. In combination, these measurements are used to determine the total dissolved solids in a liquid using a mathematical relationship for expressing the relationship between variables. Furthermore, additional mathematical relationships are provided for estimating the relative contribution of inorganic and organic dissolved components, or ionic and non-ionic components.

According to a specific object of the invention an on-line measurement and control system for dissolved substances in paper mill process waters is provided. Environmental concerns and demanding manufacturing processes afford the development of sensors. In accordance with the invention the amount of dissolved solids is measured as a function of both UV absorbance and conductivity of the sample. High levels of dissolved solids and variation in the amount of dissolved solids leads to runability problems of paper machines. Thus, to improve the manufacturing process in a pulp and paper mill better control of the amount of dissolved solids in process water, such as white water, is needed.

SUMMARY OF THE INVENTION

A method for determining an amount of dissolved matter in a liquid sample is provided in accordance with the invention, comprising the steps of:

(a) irradiating at least a portion of the liquid sample with light of at least a first wavelength within a range of wavelengths in an ultraviolet region, wherein said range of wavelengths is for allowing an absorption measurement of said liquid sample;

(b) measuring an absorption of the first wavelength by the liquid sample;

(c) measuring a conductivity of the liquid sample; and (d) computing the amount of dissolved matter in the liquid sample from a first relationship between the measured absorption of the first wavelength by the liquid sample and the measured conductivity of the liquid sample using a suitably programmed processor.

In accordance with another aspect of the invention an apparatus is provided for determining an amount of dissolved matter in a liquid sample comprising:

(a) an ultraviolet detection unit for measuring an absorption of at least a first wavelength within a range of wavelength in an ultraviolet region, said ultraviolet detection unit for measuring the absorption by the liquid sample;

(b) a conductivity unit for measuring a conductivity of the liquid sample; and (c) a suitably programmed processor for determining a first relationship between the absorption of the first wavelength by the liquid sample and the conductivity of the liquid sample for computing the amount of dissolved solids in the liquid sample.

In accordance with the invention there is further provided a method for controlling an amount of dissolved solids in a process water from pulp and paper processing using one of a counter-current flow process and a discrete chemical treatment process comprising the steps of:

(a) measuring an absorbance of the process water at a first wavelength within a range of wavelength in an ultraviolet region;

(b) measuring the conductivity of the process water; and (c) determining the amount of dissolved solids in the process water from a first relationship in dependence upon the measured absorbance and the measured conductivity.

BRIEF DESCRIPTION OF THE DRAWINGS

Exemplary embodiments of the invention will now be described in accordance with the drawings in which.

DETAILED DESCRIPTION OF THE INVENTION

Figure 1:
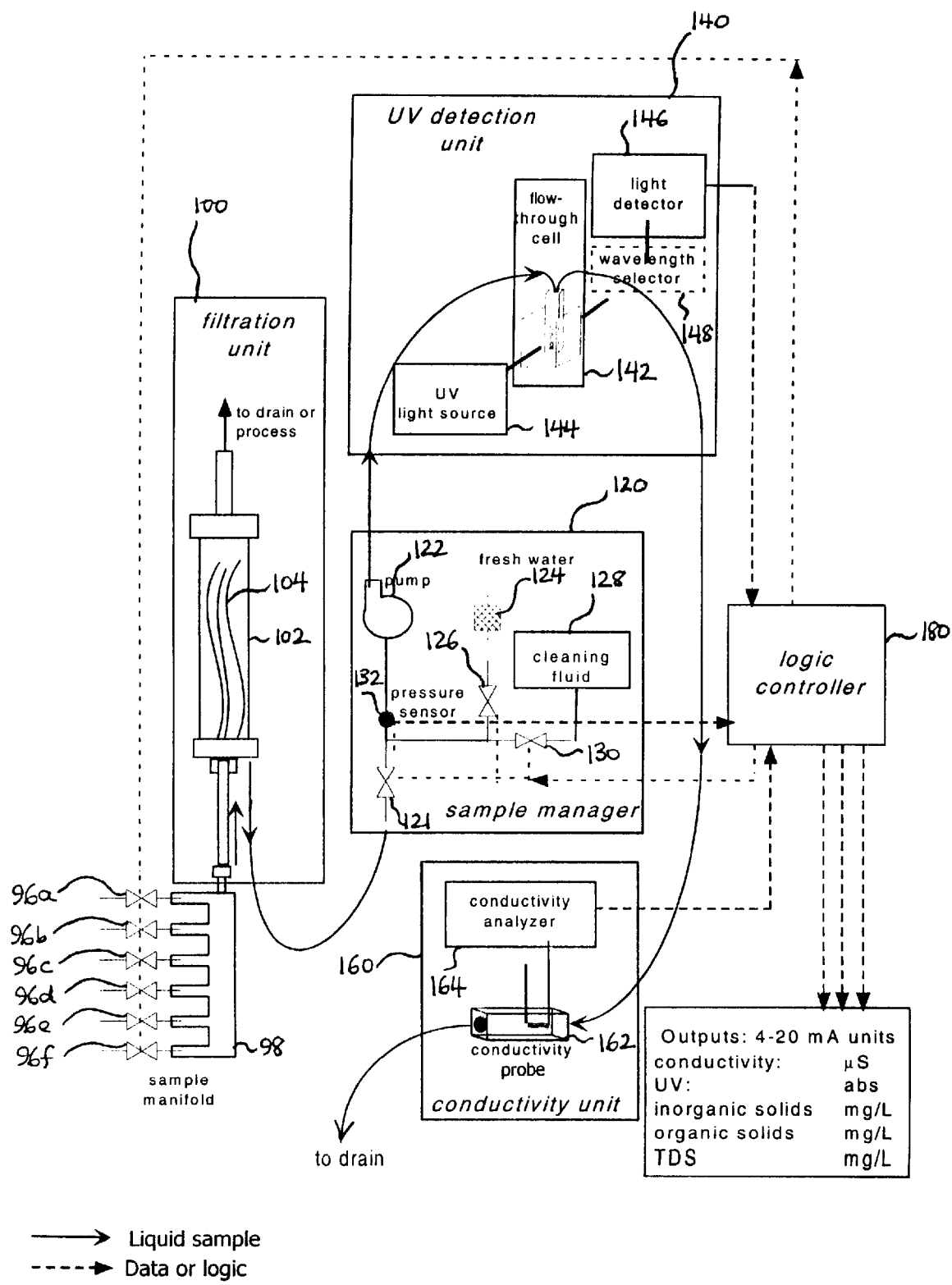
FIG. 1 is a schematic diagram of the Dissolved Solids Analyzer.

The method and the apparatus in accordance with the invention provides for on-line measurements of dissolved solids in a liquid sample. This invention is particularly useful for determining or estimating the amount of dissolved solids in pulp or paper mill process water or effluents. Referring now to FIG. 1, a schematic diagram of the dissolved solids analyzer is shown. The flow of the liquid sample is shown as solid black lines and the data flow is shown as dashed lines. A liquid sample is introduced into the sample manifold 98 by opening an inlet valve 96. In a preferred embodiment, the apparatus in agreement with the invention has a plurality of inlet valves 96a–f, as shown in FIG. 1, for receiving samples from a plurality of processes in an integrated pulp and paper mill. Valves 96a–f are in communication with a logic controller 180 for controlling the delivery of liquid samples to the sample manifold 98. The sample manifold 98 is in communication with a filtration unit 100. The function of the filtration unit 100 is to filter the liquid sample in a reproducible manner for removing particulates therefrom. The liquid sample is passed through a Minworth Systems (MSL) filtration unit 102 with "Zeeweed" hollow fiber microfilter 104 manufactured by Zenon Labs. This system has automated continuous cleaning and back-flushing. The filter 102 works for white water at temperatures of 45° C. and below. Those skilled in the art will appreciate that another filtration system may serve in place of the Zenon Labs hollow fiber microfilter. In order to obtain a reproducible measurement the filter 102 is chosen to be of the cross-flow type or tangential-flow type with the flow across the membrane being 20–100 times the flow through the membrane. Furthermore, the filter should be regularly backed-pulsed with the filtrate to ensure minimal accumulation of suspended solids on the filter surface. Filtering through a filter cake leads to unreliable ultraviolet (UV) measurements of a pulp or paper mill process water because an accumulating filter cake consisting of pulp fiber, fines and colloids will result in the selective removal of some dissolved substances. Filters which utilize the cross-flow principle to minimize filter cake formation are for example tubular membrane filters by Koch Membrane Systems, Inc. and sintered metal filters by Mott Industries. However, the liquid samples may also be manually introduced into the system through a sample port.

After the liquid sample is filtered in the filtration unit 100 it is directed to the sample manager 120. The sample manager consists of a valve 121 for delivering the filtered liquid sample to the UV detection unit 140 and the conductivity unit 160, a valve 126 for delivering fresh water from the fresh water reservoir 124 to the Uw detection unit 140 and the conductivity unit 160, a valve 130 for delivering a cleaning fluid from the cleaning fluid reservoir 128 to the UV detection unit 140 and the conductivity unit 160, a pump 122 for delivering the liquid sample, the fresh water or the cleaning fluid from the sample manager 120 to the UV detection unit 140 and the conductivity unit 160, and a pressure sensor 132. Valves 121, 126, 130, and the pressure sensor 132 are in communication with a logic controller 180. The pressure sensor 132 provides feedback to the logic controller 180 for controlling a cleaning cycle.

The pump 122 delivers the liquid sample to the UV detection unit 140. In the UV detection unit 140, the liquid sample is passed through a flow-through cell 142. This flow-through cell 142 is irradiated with UV light provided by a UV light source 144 located on one side of the flow-through cell 142. A light detector 146, located on another side of the flow-through cell 142, measures the absorbance of UV light as it traverses the liquid sample. The light detector 146 is connected to a wavelength selector 148 and the logic controller 180. The raw data of UV light absorbance by the liquid sample is passed from the light detector 146 to the logic controller 180 for further data processing. In a preferred embodiment a variable wavelength UV-visible spectrophotometer is used, such as a Shimadzu UV-visible HPLC detector set, or a D-star DFW-20/21 detector. The UV detector may be purchased as an assembled unit or manufactured within an integrated dissolved solids detection system. Many single (fixed) wavelength or selectable wavelength UV-visible spectrophotometers are commercially available. However, the most important components of the UV detection unit 140 are:

i) the light detector 146, such as a silicon photovoltaic detector (Siemens) or a photomultiplier;

ii) the wavelength selector 148, such as a monochromator or a 280 nm interference filter for 280 nm (Oriel, Edmond Scientific);

iii) the UV light source 144, such as a deuterium lamp or a xenon arc light source, examples include McPherson, EGG, Ocean Optics, ILC;

iv) the flow-through cell 142, such as a 1 mm quartz or Suprasil flow-through cell (Helma, 170.000)

The UV detection unit is in its preferred embodiment temperature controlled with high quality power supplies for the UV light source and the light detector.

The preferred wavelength for measuring the UV absorbance is 280 (±2) nm. However, a wavelength range between 205–380 nm produces suitable results.

After passing through the UV detection unit 140 the liquid sample is delivered to the conductivity unit 160. This conductivity unit 160 consists of a conductivity probe 162 and a conductivity analyzer 164. The conductivity probe 162 is a flow-through contact probe with a cell constant of 1. The specifications for the conductivity analyzer 164 are as follows:

Ranges: Conductivity (switchable)

0 to 19.99 mS/cm 0 to 1999.9 $\mu$S/cm 0 to 199.9 $\mu$S/cm

Temperature range 0 to 100° C.

Resolution: Conductivity 1 $\mu$S/cm

Temperature 0.1° C.

Accuracy: Conductivity +/–0.5%

Temperature 0.5° C.

Temperature compensation 0 to 100° C.

Excitation frequency 1 kHz

Reference temperature 0 to 100° C.

Cell constant 0.2 (programmable)

Examples of suitable conductivity analyzers that can be used in the apparatus shown in FIG. 1 are GLI Model C33, the IC Controls conductivity analyzer, the Honeywell 9782 Analyzer, and the Hach Model 471 conductivity analyzer. The conductivity unit 160 is connected to the logic controller 180 and the raw data obtained from conductivity measurements of the liquid sample are delivered from the conductivity analyzer 164 to the logic controller 180 for further data processing.

Conductivity, also called specific conductance ($\kappa$), is the conductance compensated for the area of the electrodes A and the distance between the electrodes l. These constants that are related to the measurement process rather than the intrinsic property of the medium are often lumped together as a cell constant.

$\theta = l/A$

Specific conductance measurement for pulp and paper process waters often will average around 1000 S cm$^{-1}$, and may range between 400–40000 S cm$^{-1}$. The cell constant for paper machine white water should be between 1.0 and 10.0. The conductance may be written as $G = \kappa l/A = \kappa/\theta$ or the conductivity may be written as $\kappa = \theta/R$ The proper units for conductivity are S cm$^{-1}$. Conductivity measurements are typically made using an AC current cycling between 60–1000 Hz with plantinized platinum electrodes and a modified Wheatstone bridge. Non-contact, toroidal conductivity probes are sometimes used to avoid electrode fouling under heavy fouling conditions. Conductivity is temperature sensitive and measurements are normally temperature compensated.

Alternatively, if desired, the conductivity unit is placed between the sample manifold 98 and the filtration unit 100 as the conductivity measurement is not influenced by the filtration process.

The logic controller 180 is a programmable unit which drives the components of the apparatus presented in FIG. 1 in a predetermined sequence. This logic controller 180 provides six 24 V DC outputs for controlling the valves 96a–f, 121, 126, 130 and the pump 122 as well as six analog inputs/outputs for the light detector 146, the pressure sensor 132 and the conductivity analyzer 164. An example for a possible logic controller to be used in the invention is the Allen Bradley 5/03 PLC. A smaller logic controller, such as the Allen Bradley Micrologix 1000 also fulfills the requirements for the logic controller 180. However, the system logic and the data acquisition system could be custom designed and manufactured.

In one embodiment the raw data obtained from the light detector 146 and the conductivity analyzer 164 are directly delivered to a Foxboro Distributed Control System (D.C.S.). There they can be accessed through the Aspen Technologies' Process Management Information System (PMIS) using a Process Explorer software.

After a liquid sample has been passed through the apparatus shown in FIG. 1 for determining the amount of dissolved solids in the liquid sample it is advantageous to perform a cleaning cycle. The logic controller 180 is opening/closing valve 126 for flushing the apparatus with fresh water, valve 130 for flushing the apparatus with a cleaning fluid and valve 121 for preventing the liquid sample from being delivered to the UV detection unit 140 and the conductivity unit 160 when a cleaning cycle is performed. The pressure sensor 132 provides the feedback to the logic controller 180 for controlling the cleaning cycle, i.e. it provides the logic controller with the information which valves are to be opened/closed. Pump 122 delivers the fresh water or the cleaning fluid to the UV detection unit 140 and the conductivity unit 160.

In the specification the determination of dissolved matter can be expressed as either an exact quantity of measured/computed (via a UV and conductivity product) of dissolved matter or alternatively the relative quantity can be expressed in form of a UV conductivity ratio.

In accordance with the invention the total amount of dissolved solids (TDS) in the liquid sample is determined from a mathematical relationship combining the UV absorbance and the conductivity measurements of the liquid sample. There is an excellent correlation between the total amount of dissolved solids (TDS) and a combination of conductivity and UV measurements. Several mathematical relationships appear to give good results for accurately predicting the TDS from a UV and conductivity measurement. The empirical relationship is set and may be updated by multilinear correlation of the UV absorbance and conductivity with measured TDS. Typically, one of the following mathematical relationships for white water filtered at 0.45 microns is used:

Paper Machine 5 White water $$TDS = 851.97 + 2.037 * Conductivity * UV_{280} \text{ Multiple } R = 0.887$$

Paper Machine 5 White water $$TDS = 2303.59 * UV_{280} + 0.918 * Conductivity + -$$

$0.422*UV_{280}*Conductivity$

Figure 2:
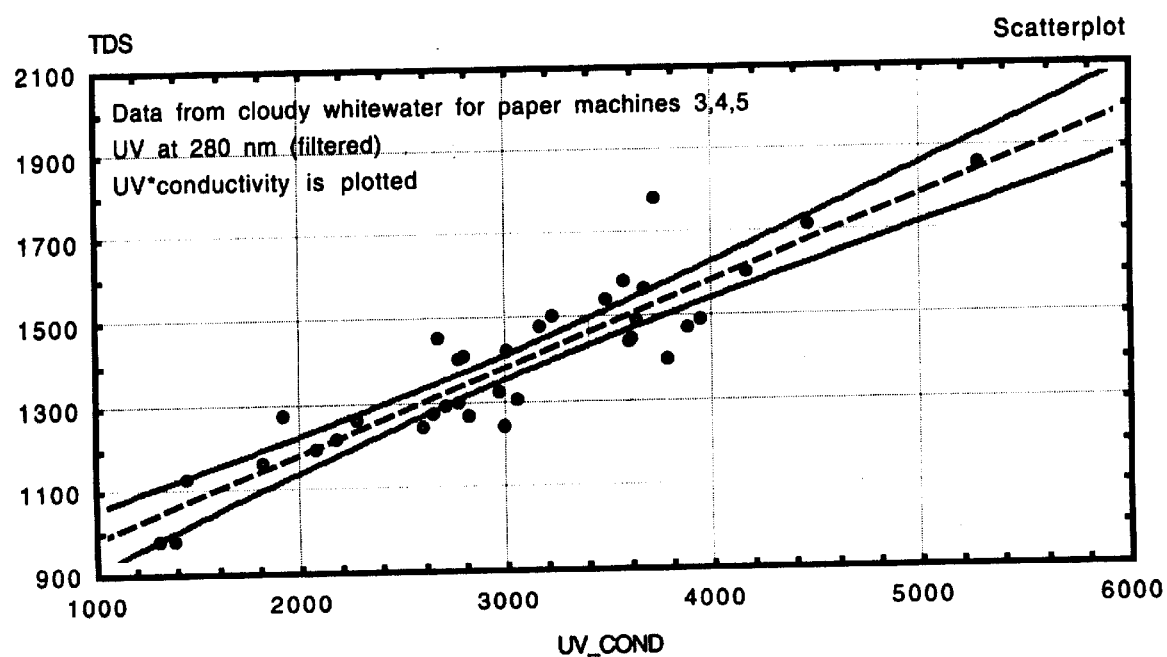
FIG. 2 presents a scatterplot of the amount of total dissolved solids versus the product of UV absorbance and conductivity.
Figure 3:
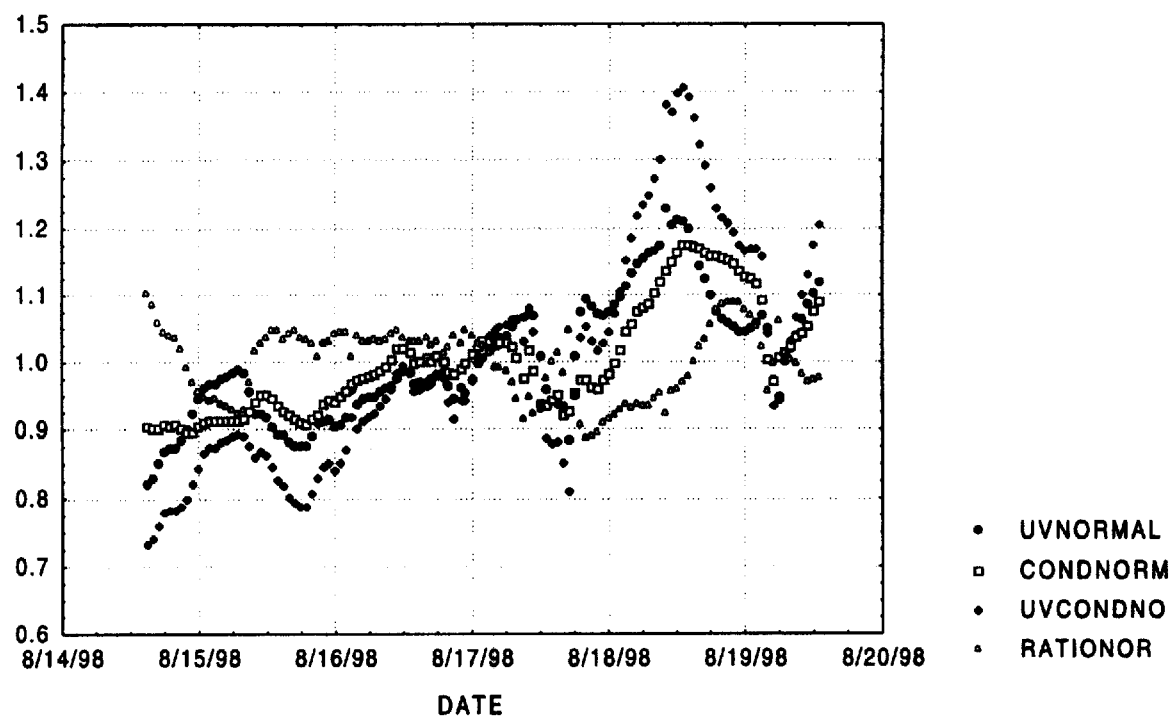
FIG. 3 shows a scatterplot presenting normalized data from the dissolved solids analyzer.

The relationship between TDS and UV absorbance and conductivity is relatively constant over extended periods in the paper mill. Using the data from paper machine 3white water (3ww), paper machine 4 white water (4ww), and paper machine 5 white water (5ww) for the period between Apr. 9–28, 1996 the following relations are obtained:
For 3ww, 4ww, 5ww combined $TDS_{pred}=788.79+0.19899*UV_{280}*Conductivity R=0.9028$ $TDS_{pred}=177.77+0.5398*Conductivity+266.09*UV_{280} R=0.9033$ For 3ww $TDS_{pred}=810+0.1855*UV_{280}*Conductivity R=0.865$ $TDS_{pred}=259+0.5301*Conductivity+191.55*UV_{280} R=0.865$ For 4ww $TDS_{pred}=774+0.20335*UV_{280}*Conductivity R=0.930$ $TDS_{pred}=109.25+0.5161*Conductivity+259.62*UV_{280} R=0.9563$ For 5ww $TDS_{pred}=788.8+0.1814*UV_{280}*Conductivity R=0.857$ $TDS_{pred}=547+0.59508*Conductivity+94.66*UV_{280} R=0.844$ This is presented in FIG. 2 showing a scatterplot of the amount of total dissolved solids versus the product of UV absorbance and conductivity. FIG. 3 shows a scatterplot presenting normalized data, i.e. divided by the average, from the dissolved solids analyzer showing relative conductivity, UV measurements, the product of UV*conductivity, and the ratio WV/conductivity. The product of UV*conductivity (UVCONDNO) shows the greatest relative variation and thereby provides a more comprehensive measure of accumulation of dissolved matter as compared to the individual UV and conductivity measurements. The ratio of the UV and conductivity measurements may deviate from its normal value when the relative contribution of the inorganic and organic components is shifted. FIG. 3 shows the gradual accumulation of dissolved components over a period of time.

Figure 4:
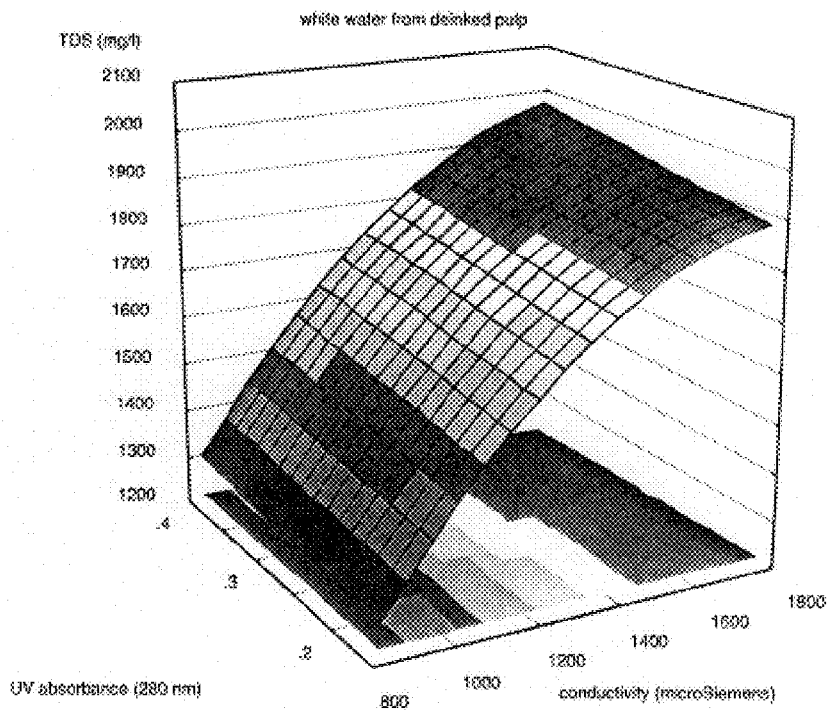
FIG. 4 presents a plot of conductivity, UV absorbance and TDS as measured from white water in deinked pulp High Density (HD) storage.
Figure 5:
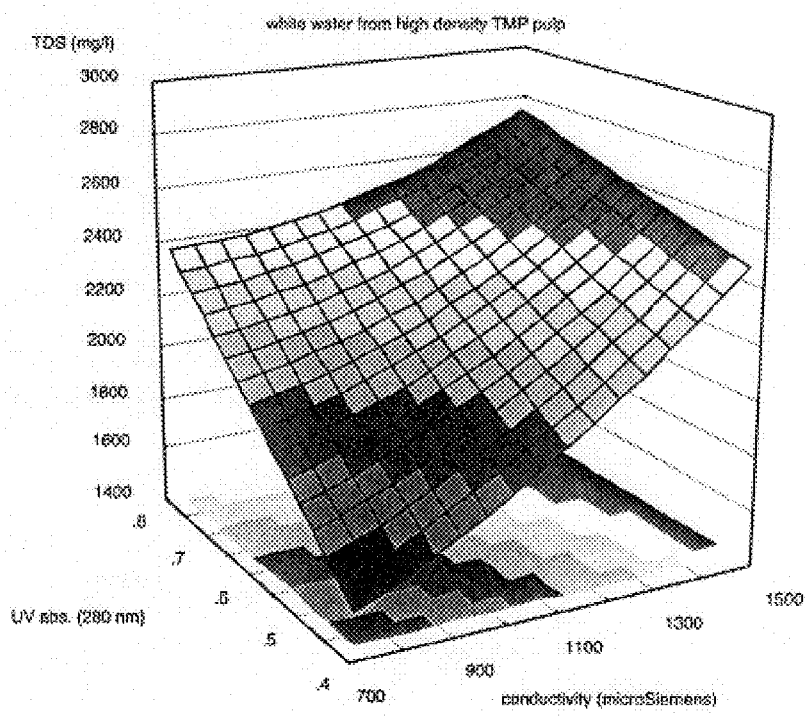
FIG. 5 presents a plot of conductivity, UV absorbance and TDS as measured from white water in TMP pulp High Density (HD) storage.
Figure 6:
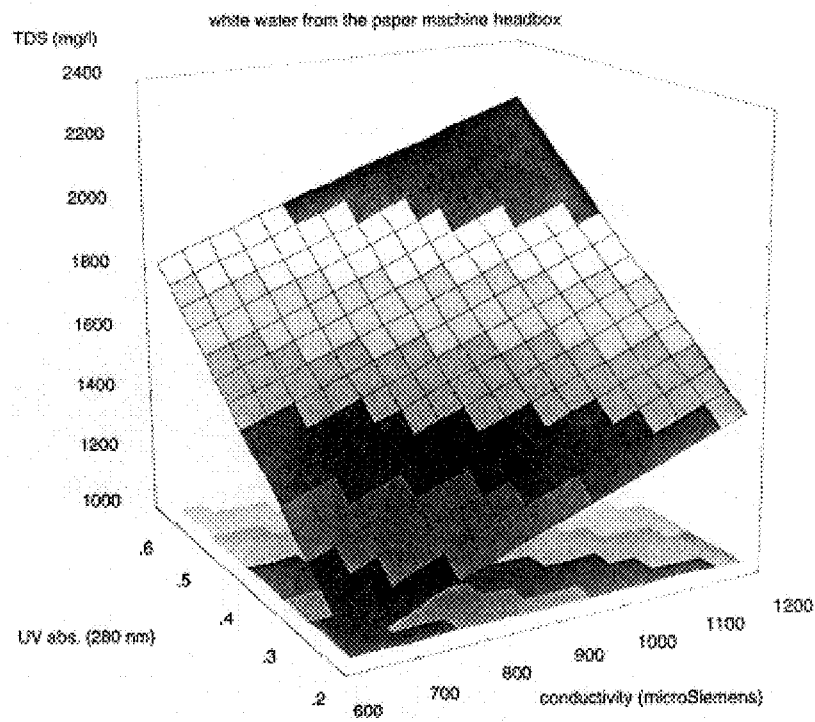
FIG. 6 presents a plot of conductivity, UV absorbance and TDS as measured from white water in the paper machine 5 headbox.

FIGS. 4–6 show three dimensional plots demonstrating the variation of TDS as a function of UV and conductivity. The variation in UV absorbance is greatest in the Thermomechanical pulp (TMP) line as shown in FIG. 5 and the variation in conductivity is greatest in the de-inked pulp line as shown in FIG. 4. The dominate contributions to the TDS are wood extractives and hemicellulose components from TMP and dissolved inorganic fillers and process chemicals from the de-inked pulp. Although these graphs look substantially different for the different testing zone the principle variation is in the amount of variation of the UV or conductivity measurement. The multiple regression of TDS against conductivity, UV and the interaction between the two (conductivity* UV) is similar but with some variation of the weighting of the conductivity and UV as a function of sampling zone.

Regression models for UV, conductivity, TDS data shown in FIGS. 4–6. At each sensor location the relationship between the TDS and the measured conductivity and UV absorbance of the filtered liquid samples has to be established and periodically tested. Several possible multiple regression models are shown for the different furnish over a three month period at the Avenor-Thunder Bay integrated pulp and paper mill. A comparison of the different models at the various locations provides some indication of how robust each of the models will be to variation in the furnish composition. Model A, with an intercept and linear coefficients on each variable is poor because of the variability in the intercept. Model B is reasonable and correct. Model C accounts for the interaction between the conductivity and UV variables. This interaction, quite high for the deinked pulp can be important from a control point of view in that it indicates that when both conductivity and UV increase there will be deposition of the dissolved substances. An important aim of a control strategy is to minimize the interaction of the various dissolved components. Model D is a simple one parameter model based on the product of the UV absorbance and conductivity. This model is probably the most robust model over time because it only involves one coefficient. In some instances, it is a benefit in having a simple model.

Head Box
A. $TDS=258+0.729*conductivity+1718*UV_{280}$
B. $TDS=0.921*conductivity+1905*UV_{280}$
C. $TDS=1.010*conductivity+2347*UV_{280}-0.675*UV_{280}*conductivity$
D. $TDS=943+1.808*UV_{280}*conductivity$ Thermomechanical Pulp
A. $TDS=426.8+0.792*conductivity+1505*UV_{280}$
B. $TDS=0.947*conductivity+1906*UV_{280}$
C. $TDS=1.194*conductivity+2219*UV_{280}-0.663*UV_{280}*conductivity$
D. $TDS=1318.8+1.322*UV_{280}*conductivity$ Deinked Pulp
A. $TDS=777+0.6576*conductivity+362.8*UV_{280}$
B. $TDS=1.036*conductivity+11309*UV_{280}$
C. $TDS=1.238*conductivity+3357*UV_{280}-2.262*UV_{280}*conductivity$
D. $TDS=1370+1.05*UV_{280}*conductivity$ Fractions of inorganic and organic dissolved solids can be determined. Inorganic dissolved solids contribute mainly to the conductivity and organic dissolved solids contribute mainly to the UV absorbance. Using the coefficients of the TDS equation the portion of TDS that is derived from the conductivity (inorganic) or the UV absorbance (organic) may be derived. This provides a good relative measure of the portions of inorganic and organic components that contribute to the total amount of dissolved solids.

The amount of organic dissolved solids is determined from their contribution to the UV term to the predicted dissolved solids terms. Thus for the above equation:

$$TDS_{organic} = \frac{2303.59*UV_{280}}{2303.59*UV_{280} + 0.918*Conductivity - 0.422*UV_{280}*Conductivity}$$

The amount of inorganic dissolved solids is determined from their contribution to the conductivity term to the predicted dissolved solids term. Thus for the above equation:

$$TDS_{inorganic} = \frac{0.918*Conductivity}{2303.59*UV_{280} + 0.918*Conductivity - 0.422*UV_{280}*Conductivity}$$

Multiple $R = 0.923$

Figure 15:
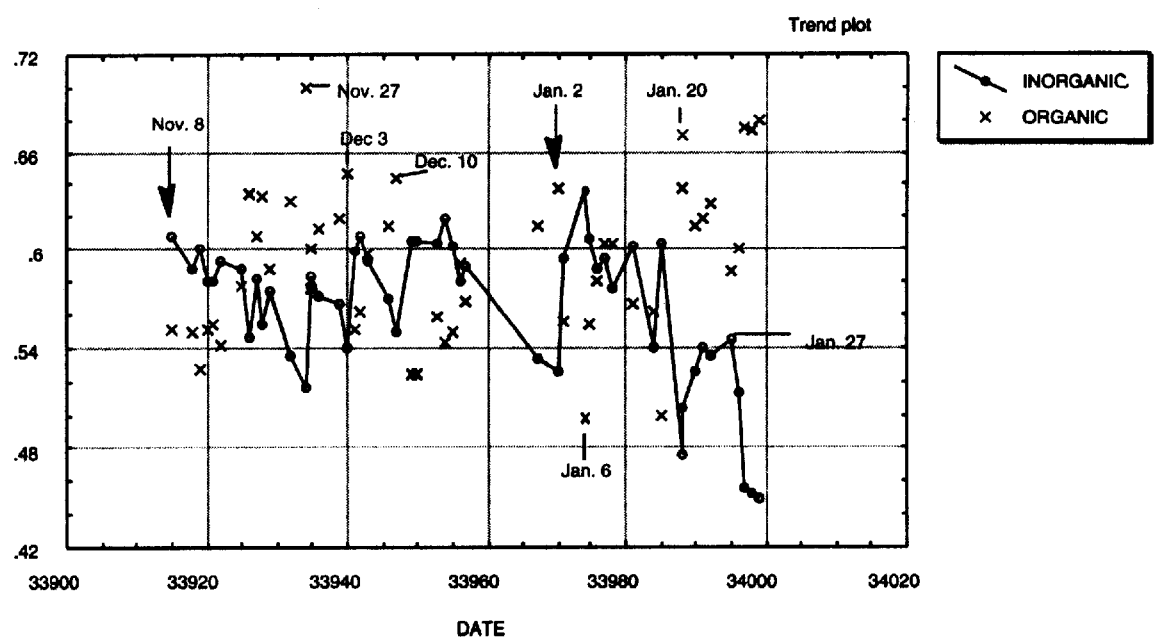
FIG. 15 is a plot showing the components of the TDS equation broken down into the UV contribution, signifying the organic portion of the TDS, and the conductivity contribution, signifying the inorganic portion of the TDS.

This is presented in FIG. 15 showing the components of the TDS equation broken down into the UV contribution, signifying the organic portion of the TDS, and the conductivity contribution, signifying the inorganic portion of the TDS. FIG. 15 further shows that there are periods when the TDS are relatively constant but the inorganic and organic portions are diverging.

Figure 7:
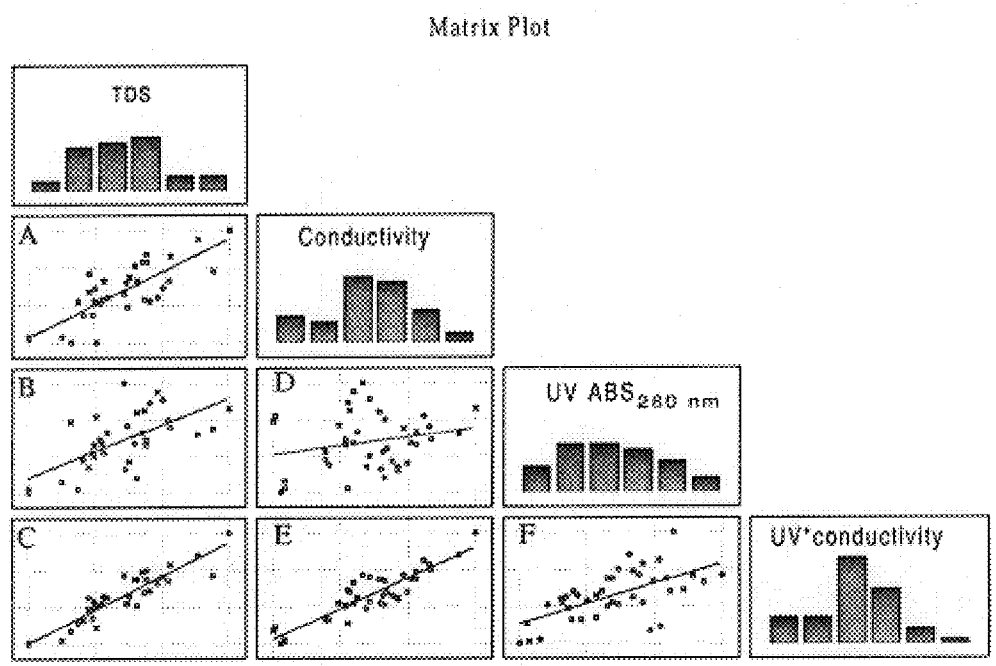
FIG. 7 presents a matrix plot showing the relationship between TDS, UV absorbance, conductivity, and the product of UV absorbance and conductivity.

The product of UV absorbance and conductivity often provides the best single measure of the amount of total dissolved solids. This is seen in FIG. 7 presenting a matrix plot showing the relationship between TDS, UV absorbance, conductivity, and the product of UV absorbance and conductivity. The measurements were taken from paper machine white water. The ordinate (y-axis) of each plot shows the relative intensity of the measurement shown in the bar chart to the right of the plot. The abscissa (x-axis) is a measure of the intensity of the measurement shown in the bar chart above the scatter plot. It is apparent that both conductivity (graph A) and UV absorbance (graph B) provide only a rough measure of the total amount of dissolved solids. Furthermore, the correlation between conductivity and UV absorbance (graph D) is poor. However, the combined measurement of UV absorbance and conductivity and using the product of both measurements, UV*conductivity, shows a very good correlation to the TDS and hence provides the best indirect measurement of the total amount of dissolved solids (graph C).

The product of UV absorbance and conductivity extenuates extremes in variation of TDS better than a sum weighted by multiple regression coefficients. The ratio of UV absorbance to conductivity provides a good measure of the relative change in the composition of dissolved organic and inorganic components. For example, in an instance where the ionic strength increases significantly, or when one or more (high valent) cations, such as $Ca^{2+}$, $Mg^{2+}$, $Al^{3+}$, and $Fe^{2+}$, increases significantly, it is expected that dissolved and colloidal substances will be destabilized, i.e. they precipitate. At pH 5.0 model dispersions of spruce pitch are destabilized at 0.1 M NaCl and 0.001 to 0.01 M $CaCl_2$. The DLVO (Deraguin, Landau, Verwey, and Overbeek) theoretical description of these effects is often used as a model that interprets charged particle interaction in terms of screening of charge-charge interactions by high ionic strength. Counter-ion condensation, or strong binding of a layer of usually high valent cations on negatively charged colloids and macromolecules leads to charge-neutralization that destabilizes dissolved and colloidal substance dispersions. In the event of such a destabilization the turbidity will first increase due to coagulation of small charged particles or aggregation and agglomeration of dissolved and colloidal substances with inorganic cations or polymeric cations. At a critical concentration the particle size will require precipitation and fixation of colloidal components.

Figure 8:
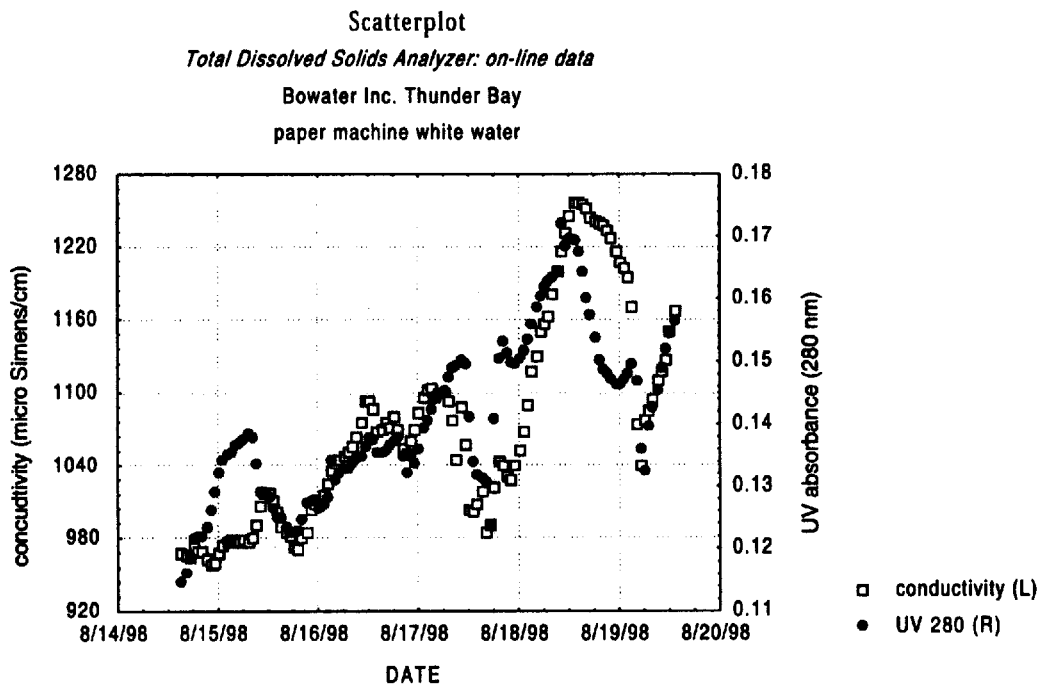
FIG. 8 presents mill data obtained with the dissolved solids analyzer showing conductivity and UV components over a period of time.

Now turning to FIG. 8, it is clear that the measures of UV absorbance and conductivity are not independent. The measurements are sometimes, but not always covariant and the components of the dissolved matter which are measured by UV absorbance and conductivity interact with each other in solution or on surfaces. FIG. 8 presents mill data from the dissolved solids analyzer showing conductivity and UV components. In this case there is significant covariance. Under these circumstances one measurement cannot substitute for the other because of the deviation from covariance. The deviation from covariance appears on August 15 when furnish rich in UV absorbing components was introduced. The deviation on August 18 is due to the more rapid response of the water system to removing UV absorbing components compared to conductive components. Both chemical and statistical arguments provide important insight into why the combined use of the two measurements is more effective in prediction of properties of a process water. From a chemical point of view, some of the UV absorbing components contribute to the conductivity. The positive covariance between conductivity and UV absorbance is a measure of the trend for one measurement to increase the other.

Figure 8A:
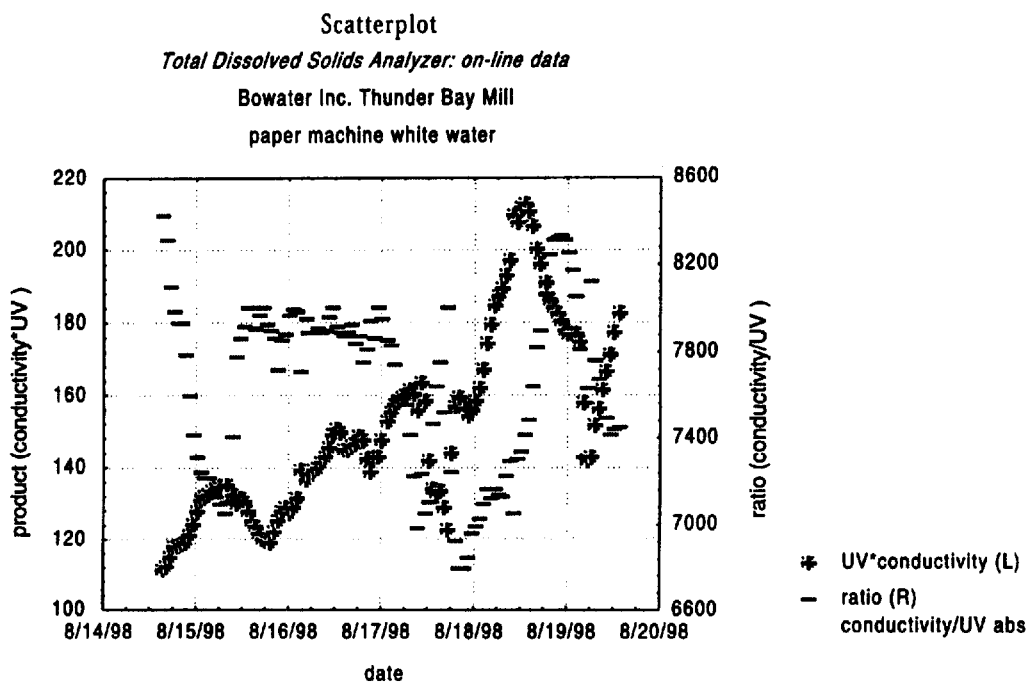
FIG. 8a shows mill data obtained with the total dissolved solids analyzer and presents a plot of the product (UV absorbance*conductivity) and the ratio (conductivity/UV) as a function of time.

FIG. 8a shows a plot of the product (UV absorbance*conductivity) and the ratio (conductivity/UV) as a function of time. The results were obtained on-line with the Total Dissolved Solids Analyzer measuring paper machine white water. The plot clearly shows that the product UV*conductivity provides the best single measurement of overall change in the amount of dissolved solids as described above. Furthermore, the plot also shows that the ratio of conductivity/UV provides a measure of the relative mixture of dissolved inorganic components.

Known components that will contribute to both UV and conductivity include resin acids, such as dehydroabietic acid, phenolic components such as gallic acid and acid lignin-carbohydrates complexes containing glucuronoxylan or arabinoglucuronoxylan. Other acidic, UV-absorbing lignin or carbohydrate derived components may be formed during an oxidative chemical process such as peroxide bleaching. During alkaline pulping and bleaching the peeling reaction results in the formation of saccharinic acid moieties on carbohydrate components.

Furthermore, some of the UV absorbing components also interact, associate or chelate the cations from the solution thus decreasing the availability of free ions to contribute to conductivity. From a statistical point of view, in any multifactor analysis of variance, factors A and B interact if the effect of factor A is not independent of the level of factor B. The model z'=A×x+B×y+C×x ×y, where z' is the predicted dependent variable (dissolved solids) and x and y are dependent variables. The beta values for coefficients A, B and C provide a measure of the relative importance of the individual terms x and y and the interaction term xy. For example, when a sample TDS is regressed against the conductivity and UV absorbance the following results are obtained:

|  | BETA | St. Err. of BETA | B | St. Err. of B | t(22) | p-level |
| --- | --- | --- | --- | --- | --- | --- |
| UV absorbance (280 nm) | .785572 | .091505 | 2921.407 | 340.2923 | 8.58499 | .000000 |
| Conductivity $\mu S\ cm^{-1}$ | .746419 | .131612 | 1.214 | .2141 | 5.67134 | .000011 |
| Interaction Term UV* conductivity | −.534150 | .116628 | −2.063 | .4504 | −4.57994 | .000146 |

In these results, the absolute value of the BETA term provides a measure of the relative importance of each term. Note that in this water sample the UV and the conductivity contribute comparably to the TDS. The interaction term shows that the interaction between the two is nearly as important, but of an opposite sense as either one of the single terms. The negative interaction term is also consistent with a chemical interaction of inorganic and organic components that occurs at high concentrations and leads to chelation, agglomeration and precipitation.

The interaction between different components in the white water may be measured using the product of UV absorbance and conductivity. When multiple regression is used to fit the TDS to a UV absorbance and conductivity measurement the Beta value obtained for the UV*conductivity product provides an expression for the interaction of the different components. The more negative the Beta value is, the more likely it is that mixing variation of one of the components will result in scaling, deposits or precipitation.

The UV absorbance provides a direct measure of lignin and a representative measure of extractives and carbohydrate components dissolved in process waters. UV absorbance is a well-known measure of the amount of lignin present. However, lignin and most lignan extractive structures have a shoulder at 280 nm that is relatively invariant with ionization of phenolic hydroxyl constituents. The extinction coefficient at 280 nm for lignin from TMP has been determined to be 17.8 L $g^{-1}$ $cm^{-1}$. Thus the UV absorbance correlates well with the TDS at different places in the paper machine even while the overall composition varies. UV absorbing dehydroabetic acid is a dominate resin acid extractive liberated from spruce wood during mechanical pulping. The relative portions of different wood extractives liberated from pulp do not vary substantially with variations in the total organic carbon (TOC) caused by recirculation of the process water. Substantial swings in pH do change the relative portions of different extractives and for this reason the calibration between UV and TOC must be location specific in a paper mill. UV lignin measurements correlate well with the biological oxygen demand (BOD) and the chemical oxygen demand (COD) from thermomechanical pulp wood material. It is now generally accepted that unpurified hemicellulose components are directly attached to lignin moieties. Hence the UV absorbance of the components attached to lignin provides a measure of the hemicellulose components. Thus the UV absorbance correlates well with the TDS at different places in the paper machine even while the overall composition varies.

Substances contributing to either UV absorbance and conductivity are known to be detrimental to papermaking. The overall build-up of dissolved solids can interfere with paper machine operations. Salts and electrolytes screen electrostatic interactions and reduce the effectiveness of cationic polymers. Also, anionic organic substances are known to lead to deposits, and reduce the paper machine runability.

Figure 9:
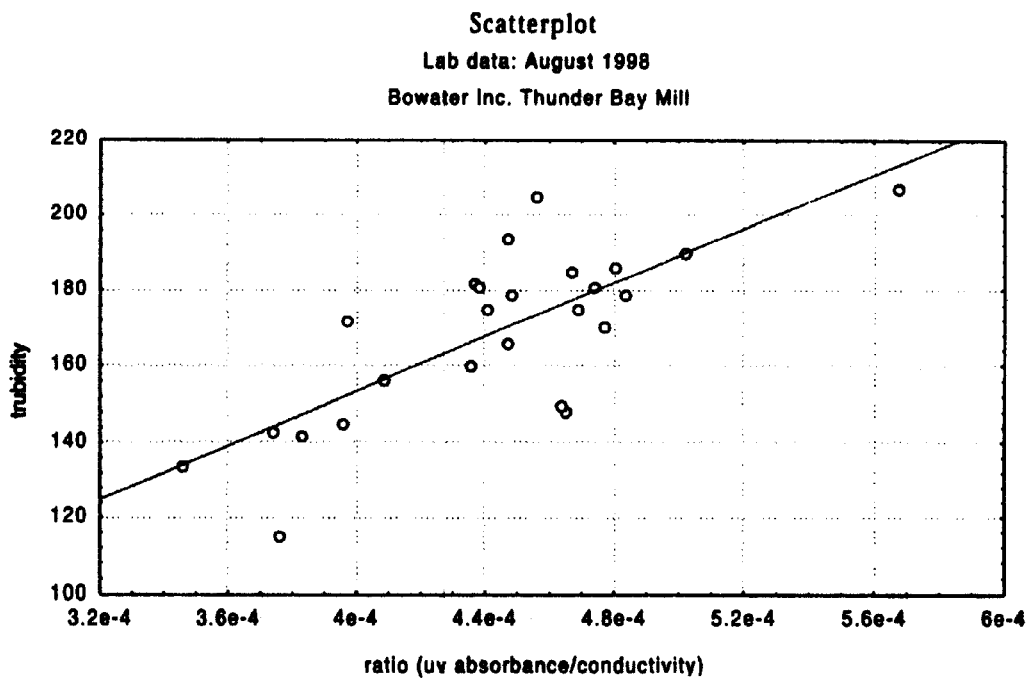
FIG. 9 shows a graph of the turbidity versus the ratio of the UV absorbance to the conductivity.
Figure 10:
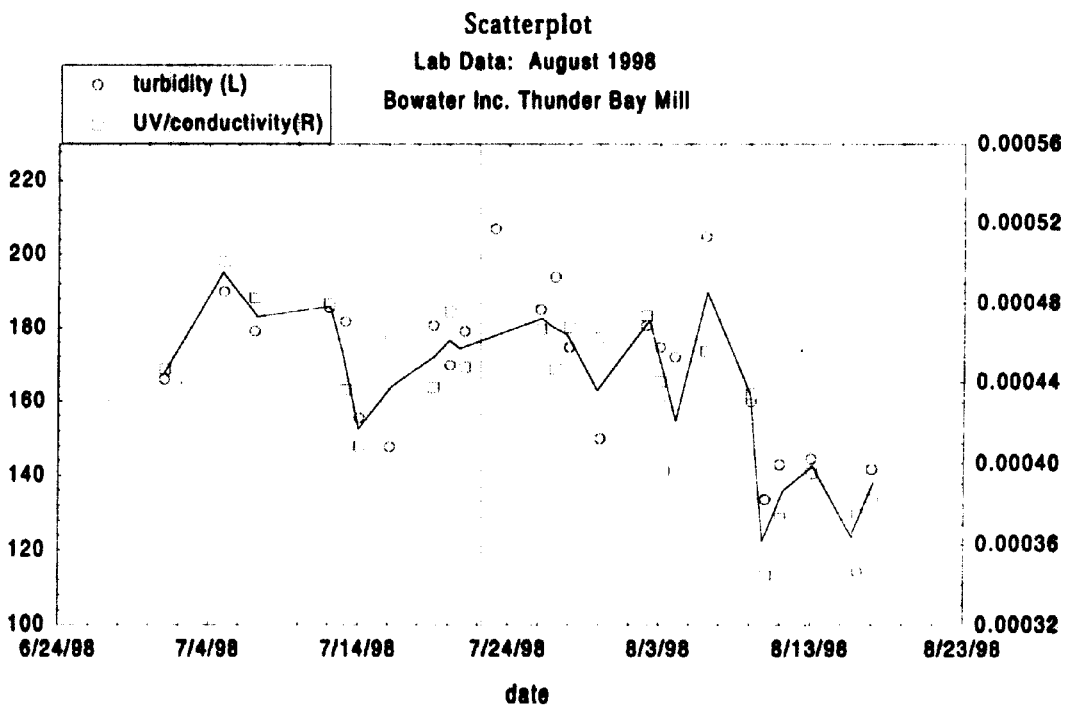
FIG. 10 shows a scatterplot of the turbidity and the ratio of the UV absorbance to the conductivity over a period of time.

The combination of anionic trash (hemicellulose, resin acids, fatty acids) as determined by UV absorbance and electrolytes as measured by conductivity are required to optimize the efficiency of cationic polymers added for fixation and retention. Turning to FIG. 9, a graph is presented showing that the ratio of the UV absorbance to the conductivity measurements correlates well with the turbidity measurement. FIG. 10 presents a scatterplot of turbidity and the ratio of the UV absorbance to the conductivity measurements over a period of approximately 2 months. This scatterplot shows clearly that the ratio of the UV absorbance to the conductivity trends well with the turbidity measurements. The relationship between the ratio of dissolved substances and the turbidity caused by colloidal particles is an indirect manifestation of the shift in the dissolved-colloidal equilibria caused by an increase in the amount of dissolved organic material contributing to colloids and a decrease in the amount of electrolytes in the water that may destabilize the colloidal substances. Turbidity has been used in the past as a means for controlling the addition of cationic fixing aids and flocculants. TOC (total organic carbon) has been used as a means to control the addition of cationic polymer and as indicated above the UV absorbance provides a representative measure of the TOC.

Figure 11:
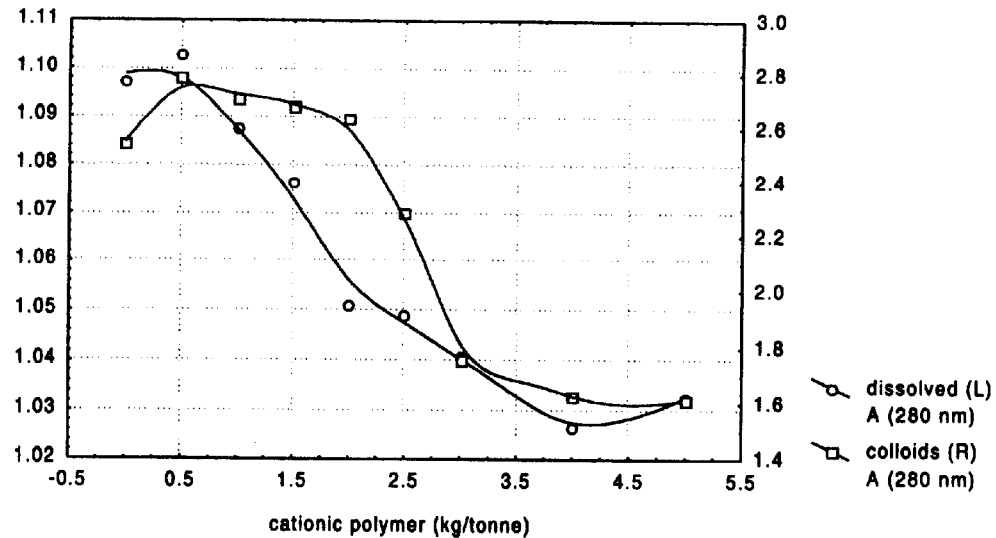
FIG. 11 shows a plot of UV absorbance of centrifuged and filtered TMP white water in dependence upon the amount of cationic polymer.
Figure 12:
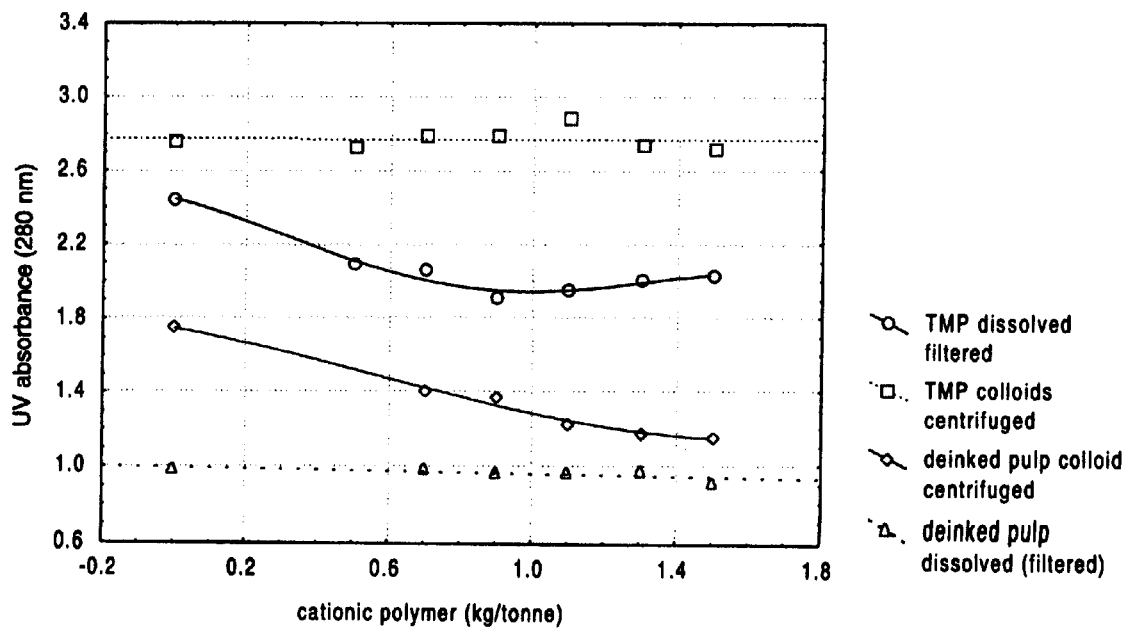
FIG. 12 presents a plot of the variation of UV absorbance as a function of added cationic polymer.

Incremental changes in the UV absorbance of dissolved solids which coincide with the variation of a cationic polymer dose provide a good measure of the interference of dissolved anionic substances to the flocculation or fixing action of an added cationic polymer. This is shown in FIGS. 11 and 12 which show results from laboratory studies and mill trials relating the variation of the UV absorbing dissolved substances to the addition of cationic polymer. FIG. 11 shows a plot of UV absorbance of centrifuiged and filtered TMP white water in dependence upon the amount of cationic polymer. This graph shows clearly the effect of added cationic polymer on the measured amount of colloids and dissolved substances. Laboratory results, as presented in FIG. 11, show that dissolved matter is removed upon the addition of cationic polymer which is used as a retention aid or fixing agent. The removal of dissolved matter is indicated by a decrease in the measured values of UV absorbance. The results are compared to the variation of colloidal substances with the addition of cationic polymer. The colloidal components are not removed until a portion of the UV-absorbing dissolved matter reacts with the polymer. FIG. 12 presents a plot of the variation of UV absorbance as a function of added cationic polymer. The results shown in FIG. 12 represent mill trial results upon polymer addition at a medium consistency pump. The mill trial clearly shows the removal of dissolved material as measured by UV absorbance upon the addition of cationic polymer used as a retention aid or fixing agent. The results are compared to the variation of colloidal substances with the addition of cationic polymer. The dissolved matter reacts with the cationic polymer in the TMP white water but not in the case of the gray water for recycled newsprint that has low concentrations of dissolved, wood-derived organic material. The results of the trial presented in FIG. 12 points out the advantages of using measurements of both dissolved and colloidal substances to control the addition of cationic polymer as a fixing agent.

Figure 12A:
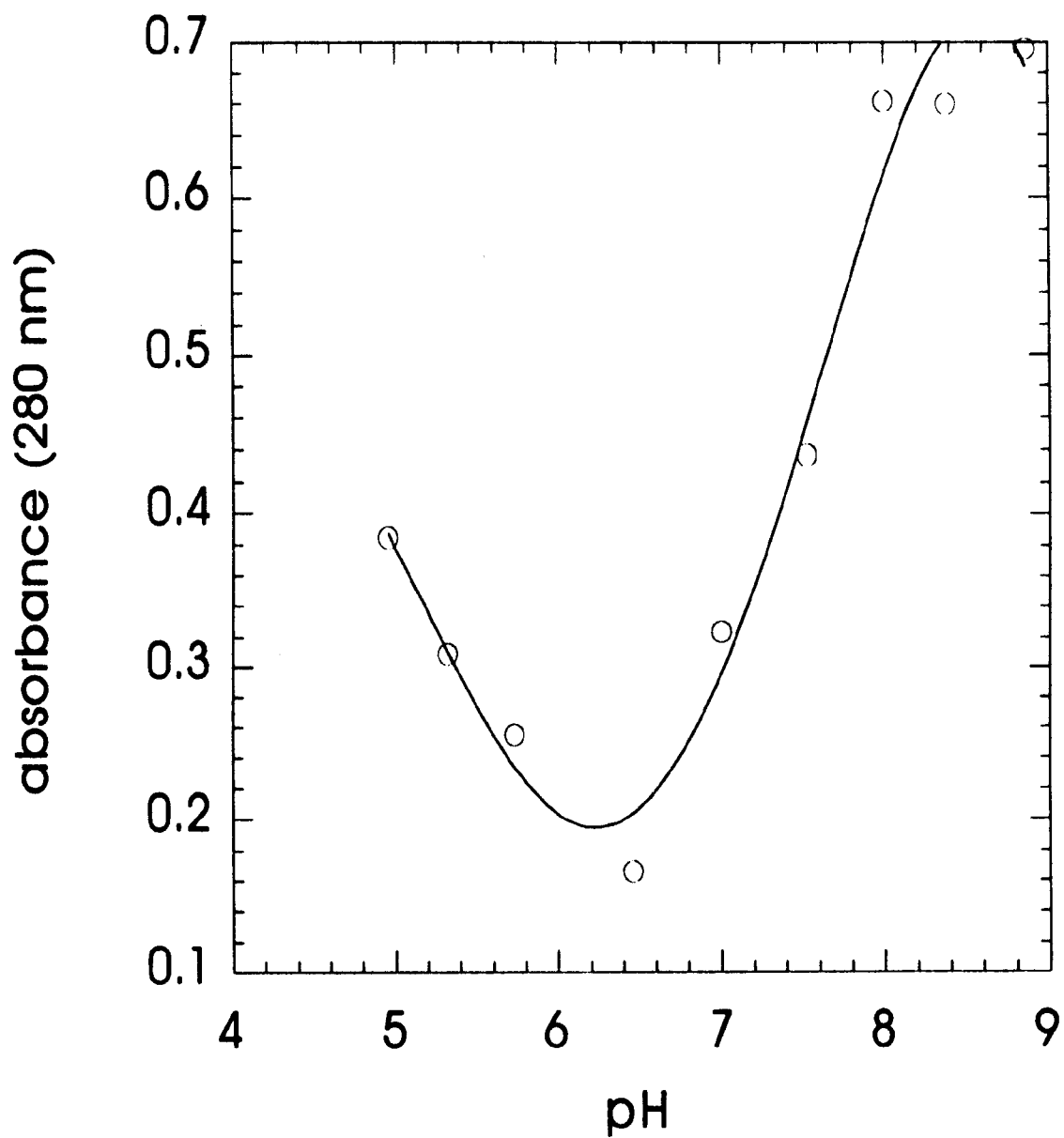
FIG. 12a shows a plot of UV absorbance vs. pH.

The UV absorbance of white water components shows a good correlation with the dissolved solids and hence UV measurements indicate the effect of changes in the pH of a liquid sample. The amount of dissolved solids is affected by altering the pH of the liquid sample, i.e. if the pH is lowered organic dissolved solids are precipitated and if the pH is increased the inorganic dissolved solids are precipitated. In application such as washing and pressing the UV absorbance provides an excellent measure of the effectiveness of the removal of potentially soluble substances. This is shown in FIG. 12a presenting a plot of $UV_{280}$ absorbance vs. pH for results obtained from a twin wire press.

The dissolved solids analyzer in agreement with the invention provides a measure of the overall change of dissolved solids in pulp or paper mill process waters or effluents. The analysis of different process streams provides a means to control both the overall level of dissolved solids using the product of the UV absorbance measurement and the conductivity measurement and the relative composition of the dissolved solids. The dissolved solids analyzer is used in various areas in pulp and paper processing, such as controlling dissolved solids in counter-current flow processes, controlling dissolved solids in pulp washing operations, reducing deposition and scaling, controlling dissolved solids in pulping operations, and controlling dissolved solids in papermaking operations.

Figure 13:
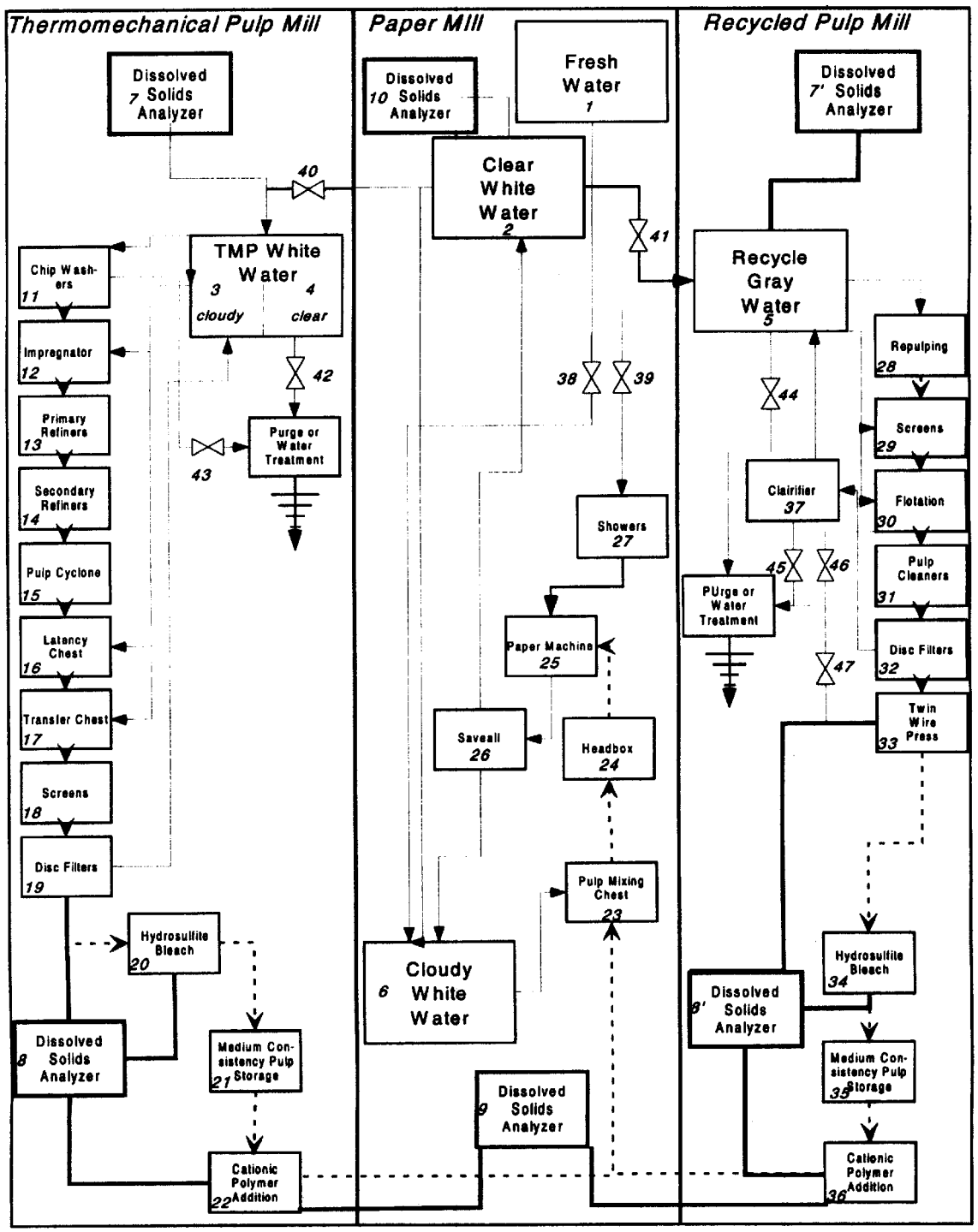
FIG. 13 presents a detailed diagram showing potential points for application of the Dissolved Solids Analyzer in an integrated pulp and paper mill.

Referring now to FIG. 13 a detailed diagram is presented showing potential points for application of the Dissolved Solids Analyzer in an integrated pulp and paper mill. In this figure, pulp flows are shown in dashed lines, water flows are shown in solid thin lines, and sampling and analysis flows for the Dissolved Solids Analyzer are shown in thick solid lines. Dissolved solids are generated in pulp mills from pulping, bleaching, addition of process chemicals and washing. The dissolved solids in paper machine white water are controlled in order to maintain a constant level of dissolved solids. Dissolved solids enrichment in pulp mills occurs during processes 11–20 in the Thermomechanical Pulp (TMP) mill and 27–33 in the deinking mill. All purging of water is done in the pulp mills. Valve 42 from chip washers 11, impregnators and chip heaters are always open. Valve 46 from the Twin Wire Press (TWP) 32, valve 47 from flotation rejects 29, and valve 44 from clarifier rejects 36 are always open. Valves 41 and 43 are open proportionally to respective pulp production rates and are supervisory controlled by Dissolved Solids Analyzers 7 and 7'. All fresh water is introduced in the paper mill. The fresh water to Paper Mill (PM) showers 26 is always open. Valve 37 (fresh water to PM white water) is used to provide feedback control to maintain a set-point for the dissolved solids. The flow rates through valves 39 and 40 are determined by water levels in tanks 4 and 5. The Dissolved Solids Analyzers 8 and 8' are used to measure a variation of dissolved solids across discrete chemical treatment processes 20 (hydrosulfite bleaching) and 22 (cationic polymer addition), or 33 (hydrosulfite bleach) and 35 (cationic polymer addition).

Figure 14:
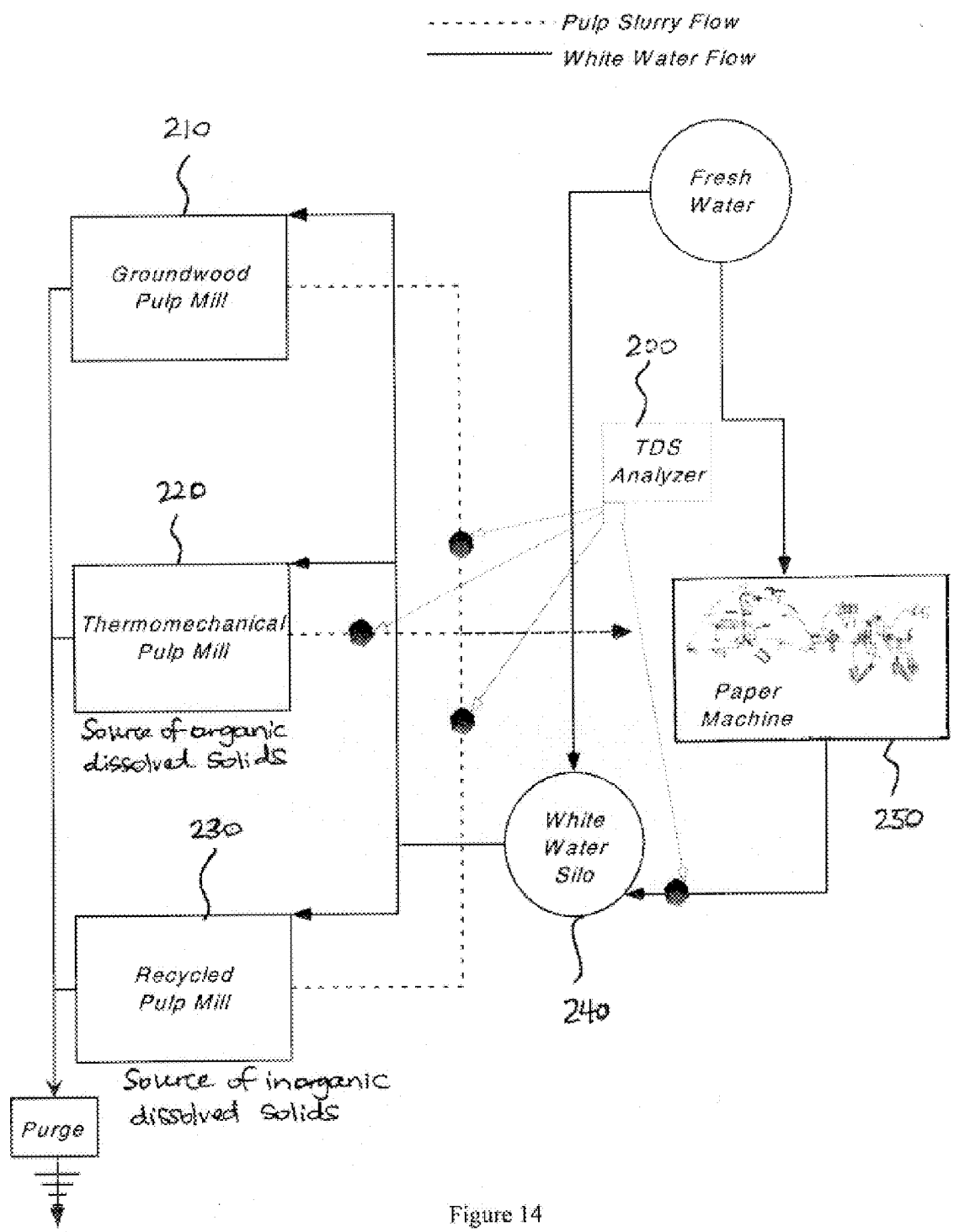
FIG. 14 presents a block diagram showing elements of measurement and the control of dissolved solids in an integrated newsprint mill.

FIG. 14 shows an example for an application of the Dissolved Solids Analyzer. A block diagram is presented showing elements of measurement and the control of dissolved solids in an integrated newsprint mill. Measurements of dissolved solids in the paper mill and pulp mill provide information to maintain the concentration and the composition of dissolved solids by varying the amount of fresh water and the relative counter-current flow to each pulp mill. In this figure, the pulp slurry flow is shown in dashed lines and the white water flow is shown in solid lines. The TDS Analyzer 200 as shown in FIG. 14 is used to determine the amount of dissolved solids in a pulp slurry flow from a Groundwood Pulp Mill 210, a Thermomechanical Pulp Mill 220, and a Recycled Pulp Mill 230. Further, the TDS analyzer is used to determine the amount of dissolved solids in a white water flow coming from a paper machine 250 to a White Water Silo 240. The Thermomechanical Pulp Mill is mostly a source of organic dissolved solids and the Recycled Pulp Mill is mostly a source of inorganic dissolved solids. An analysis of different process streams provides a means for controlling both, the overall level of dissolved solids using the product of the UV absorbance measurements and the conductivity as well as the relative composition of the dissolved solids.

The above-described embodiments of the invention are intended to be examples of the present invention and numerous modifications, variations, and adaptations may be made to the particular embodiments of the invention without departing from the scope and spirit of the invention, which is defined in the claims.

What is claimed is:

1. A method for determining an amount of dissolved matter in a liquid sample comprising the steps of:

(a) irradiating at least a portion of the liquid sample with light of at least a first wavelength within a range of wavelengths in an ultraviolet region, wherein said range of wavelengths is for allowing an absorption measurement of said liquid sample;

(b) measuring an absorption of the first wavelength by the liquid sample;

(c) measuring a conductivity of the liquid sample; and (d) computing the amount of dissolved matter in the liquid sample from a first relationship between the measured absorption of the first wavelength by the liquid sample and the measured conductivity of the liquid sample using a suitably programmed processor, said first relationship includes at least one of a product and a ratio of said measured conductivity and absorption.

2. A method as defined in claim 1 wherein the first relationship is determined by performing regression analysis by utilizing the measured conductivity and absorption.

3. A method as defined in claim 2 wherein the first relationship is a sum including at least one of a product and a ratio of said measured conductivity and absorption.

4. A method as defined in claim 3, wherein the amount of dissolved matter includes an amount of dissolved organic matter and an amount of dissolved inorganic matter.

5. A method as defined in claim 4, wherein the amount of dissolved organic matter is determined from a ratio including the absorption of the first wavelength to the first relationship.

6. A method as defined in claim 4, wherein an amount of dissolved inorganic matter is determined from a ratio of the conductivity to the first relationship.

7. A method as defined in claim 1 wherein the first relationship is described by a following equation and wherein the processor computes the amount of dissolved matter from said equation:

$$\text{dissolved matter} = A*\text{conductivity} + B*\text{ultraviolet absorption} + C*\text{conductivity}*\text{ultraviolet absorption}$$

wherein A, B, and C are factors determined by regression analysis.

8. A method as defined in claim 1, further comprising the step of substantially removing an amount of colloidal particles in the liquid sample for lessening an unwanted effect of an interaction between at least some colloidal particles and the irradiating light.

9. A method as defined in claim 1, wherein the range of wavelength in the ultraviolet region is from 205 nm to 380 nm.

10. A method as defined in claim 9, wherein the first wavelength is substantially 280 (±2) nm.

11. An apparatus for determining an amount of dissolved matter in a liquid sample comprising:

(a) an ultraviolet detection unit for measuring an absorption of at least a first wavelength within a range of wavelength in an ultraviolet region, said ultraviolet detection unit for measuring the absorption by the liquid sample;

(b) a conductivity unit for measuring a conductivity of the liquid sample; and (c) a processor for determining a first relationship between the absorption of the first wavelength by the liquid sample and the conductivity of the liquid sample for computing the amount of dissolved matter in the liquid sample, said first relationship includes at least one of a product and a ratio of the measured conductivity and absorption.

12. An apparatus as defined in claim 11, wherein the processor is programmed to solve the following equation:

$$\text{dissolved matter} = A*\text{conductivity} + B*\text{ultraviolet absorption} + C*\text{conductivity}*\text{ultraviolet absorption}$$

wherein A, B, and C are factors determined by regression analysis.

13. A method for controlling an amount of dissolved solids in a process water from pulp and paper processing using one of a counter-current flow process and a discrete chemical treatment process comprising the steps of:
 (a) measuring an absorbance of the process water at a first wavelength within a range of wavelength in an ultraviolet region;
 (b) measuring the conductivity of the process water; and
 (c) determining the amount of dissolved solids in the process water from a first relationship in dependence upon the measured absorbance and the measured conductivity, said first relationship includes at least one of a product and a ratio of said measured absorbance and conductivity.

14. A method as defined in claim 13 wherein the first relationship is determined by performing regression analysis by using the measured conductivity and absorbance.

15. A method as defined in claim 14 wherein the first relationship is described by a following equation:

$$\text{dissolved solids} = A*\text{conductivity} + B*\text{ultraviolet absorption} + C*\text{conductivity}*\text{ultraviolet absorption}$$

wherein A, B, and C are factors determined by regression analysis.

16. A method as defined in claim 14 wherein the first relationship is a sum including at least one of a product and a ratio of said measured conductivity and absorption.

17. A method as defined in claim 14 wherein the amount of dissolved solids includes an amount of dissolved organic solids and an amount of dissolved inorganic solids.

18. A method as defined in claim 17, wherein the amount of dissolved organic solids is determined from a ratio of the absorption of the first wavelength to the first relationship.

19. A method as defined in claim 17, wherein the amount of dissolved inorganic solids is determined from a ratio including the conductivity to the first relationship.

20. A method as defined in claim 13 further comprising the step of substantially removing an amount of colloidal particles in the process water for lessening an unwanted effect of an interaction between at least some colloidal particles and the absorbance.

21. A method as defined in claim 13 wherein the discrete chemical treatment process includes adding cationic polymer to the process water for removing dissolved organic solids therefrom.

22. A method as defined in claim 13 wherein the amount of dissolved solids in the process water is controlled by changing a pH of said process water for one of removing dissolved organic solids and dissolved inorganic solids.

23. A method as defined in claim 13 wherein the range of wavelength is from 205 nm to 380 nm.

24. A method as defined in claim 23 wherein the first wavelength is substantially 280 (±2) nm.

25. A method for determining an amount of dissolved matter in a liquid sample comprising the steps of:
 (a) irradiating at least a portion of the liquid sample with light of at least a first wavelength within a range of wavelengths in an ultraviolet region, wherein said range of wavelengths is for allowing an absorption measurement of said liquid sample;
 (b) measuring an absorption of the first wavelength by the liquid sample;
 (c) measuring a conductivity of the liquid sample; and
 (d) determining the amount of dissolved matter in the liquid sample from a first relationship between the measured absorption of the first wavelength by the liquid sample and the measured conductivity of the liquid sample, said first relationship includes at least one of a product and a ratio of said measured absorbance and conductivity.

* * * * *

UNITED STATES PATENT AND TRADEMARK OFFICE
CERTIFICATE OF CORRECTION

PATENT NO. : 6,134,952

DATED : October 24, 2000

INVENTOR(S) : Garver et al.

It is certified that error appears in the above-identified patent and that said Letters Patent is hereby corrected as shown below:

Front page:
    Title should read: -- DISSOLVED SOLIDS ANALYZER --,
    *Attorney, Agent, or Firm*: "Neil Teitelbaum & Associates" should read -- Freedman & Associates --.

Drawing sheet 7, Figure 9: y-axis legend should read -- turbidity --.

Drawing sheet 8 Figure 11: last word of the figure title should read -- substances --.

Col. 2, line 52: delete "U.S.".

Col. 6, line 39, "Uw" should read -- UV --.

Col. 7, line 62: formula " $G=\kappa l/A=\kappa/\theta$ " should read: $G=\kappa l/A=\kappa\theta$.

Col. 9, line 1: "0.422" should read -0.422,
    line 35, "WV" should read -- UV --.

Col. 12, line 52: above the table, please insert the following:
-- Stepwise Forward Multiple Regression: Summary for Dependent Variable: TDS
R=.99897481  $R^2$=.99795066 Adjusted $R^2$=.99767121
F(3,22)=3771.1 p<.00000 Std. Error of estimate: 74.838--.

UNITED STATES PATENT AND TRADEMARK OFFICE
CERTIFICATE OF CORRECTION

PATENT NO. : 6,134,952
DATED : October 24, 2000
INVENTOR(S) : Garver et al.

It is certified that error appears in the above-identified patent and that said Letters Patent is hereby corrected as shown below:

Col. 14, line 19: "centrifuiged" should read -- centrifuged --.

Signed and Sealed this

Eighth Day of May, 2001

Attest:

NICHOLAS P. GODICI

Attesting Officer

Acting Director of the United States Patent and Trademark Office